United States Patent
Reiz et al.

(10) Patent No.: US 10,823,322 B2
(45) Date of Patent: Nov. 3, 2020

(54) FASTENING DEVICE FOR MEASURING APPARATUSES ON PIPES

(71) Applicant: Georg Fischer Rohrleitungssysteme AG, Schaffhausen (CH)

(72) Inventors: Robert Reiz, Stühlingen (DE); Juergen Roesch, Lenzkirch (DE); Edin Hasific, Schaffhausen (CH); Marcel Graf, Neuhausen am Rheinfall (CH)

(73) Assignee: Georg Fischer Rohrleitungssysteme AG (CH)

( * ) Notice: Subject to any disclaimer, the term of this patent is extended or adjusted under 35 U.S.C. 154(b) by 0 days.

(21) Appl. No.: 16/299,921

(22) Filed: Mar. 12, 2019

(65) Prior Publication Data
US 2019/0309887 A1    Oct. 10, 2019

(30) Foreign Application Priority Data

Apr. 5, 2018  (EP) .................................... 18165894

(51) Int. Cl.
| | |
|---|---|
| *F16L 55/07* | (2006.01) |
| *G01N 33/207* | (2019.01) |
| *F16L 41/02* | (2006.01) |
| *G01N 21/952* | (2006.01) |
| *F16L 11/12* | (2006.01) |
| *B29C 65/82* | (2006.01) |
| *B29C 65/00* | (2006.01) |
| *F16L 3/08* | (2006.01) |

(52) U.S. Cl.
CPC .............. *F16L 55/07* (2013.01); *F16L 11/12* (2013.01); *F16L 41/02* (2013.01); *G01N 21/952* (2013.01); *G01N 33/207* (2019.01); *B29C 65/82* (2013.01); *B29C 65/8292* (2013.01); *B29C 66/1142* (2013.01); *B29C 66/5221* (2013.01); *F16L 3/08* (2013.01); *G01N 2201/021* (2013.01); *G01N 2201/0646* (2013.01)

(58) Field of Classification Search
CPC ......... G01N 33/207; G01F 1/66; G01F 1/662; G01F 1/667; G01F 25/0007
See application file for complete search history.

(56) References Cited

U.S. PATENT DOCUMENTS

| | | | | |
|---|---|---|---|---|
| 4,454,767 A | * | 6/1984 | Shinkai ................... | G01F 1/662 73/861.18 |
| 5,337,615 A | * | 8/1994 | Goss ....................... | G01F 1/065 73/861.33 |

(Continued)

FOREIGN PATENT DOCUMENTS

| | | |
|---|---|---|
| CN | 201397161 Y | 2/2010 |
| EP | 2963380 A1 | 1/2016 |
| WO | WO-2011/112946 A1 | 9/2011 |

*Primary Examiner* — Randy W Gibson
*Assistant Examiner* — Gedeon M Kidanu
(74) *Attorney, Agent, or Firm* — Harness, Dickey & Pierce, P.L.C.

(57) ABSTRACT

A device for fastening a measuring apparatus on pipes, in particular a butt weld seam checking measuring apparatus, containing a housing for accommodating the measuring, control, and/or drive units and a clamp, wherein the clamp is designed as a ring segment, wherein the clamp is attached in the radial direction over a pipe external diameter, wherein the clamp has a pre-tension in the installed state.

8 Claims, 5 Drawing Sheets

(56) References Cited

U.S. PATENT DOCUMENTS

Figure 1:
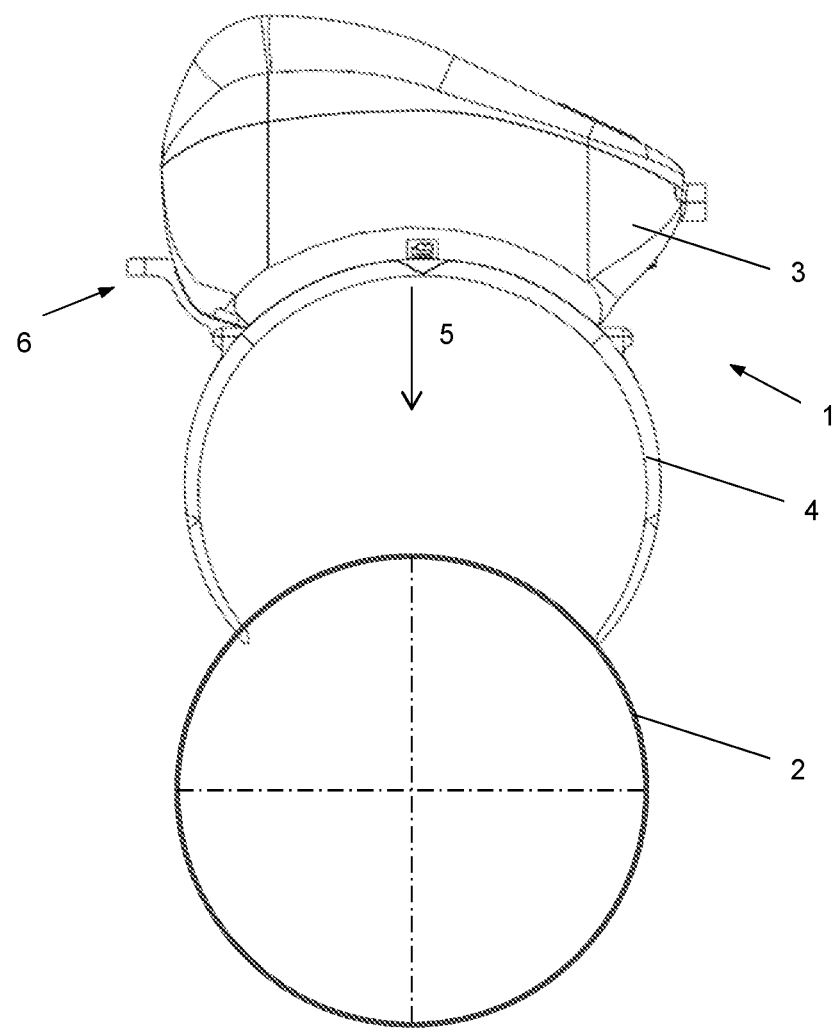

| | | | | |
|---|---|---|---|---|
| 5,615,457 A * | 4/1997 | Steinkonig | ............ | F16L 33/03 24/20 EE |
| 5,815,892 A * | 10/1998 | Geppert | ................ | F16L 23/04 24/20 R |
| 5,819,376 A * | 10/1998 | Kovalsky | ................ | F16L 33/03 24/23 R |
| D457,451 S * | 5/2002 | Chen | ............................ | D10/79 |
| 6,681,642 B2 * | 1/2004 | Ohkawa | ................. | G01F 1/662 264/295 |
| D515,953 S * | 2/2006 | Chang | ............................ | D10/79 |
| 8,438,936 B2 * | 5/2013 | Feldman | ................. | G01F 1/662 73/861.27 |
| 8,714,030 B1 * | 5/2014 | Liu | ........................ | G01F 1/662 73/861.28 |
| D715,169 S * | 10/2014 | Chen | ............................ | D10/79 |
| 9,255,641 B2 | 2/2016 | Raible | | |
| 10,035,194 B2 | 7/2018 | Hunnekuhl | | |
| 10,365,137 B2 * | 7/2019 | Forster | ................... | G01F 1/662 |
| 2003/0159255 A1 * | 8/2003 | Senovich | ................. | F16L 33/03 24/20 R |
| 2005/0184722 A1 * | 8/2005 | Gregorec, Jr. | ........... | G01R 1/22 324/126 |
| 2010/0131210 A1 * | 5/2010 | Fingerhut | .............. | G01N 27/90 702/38 |
| 2010/0148756 A1 * | 6/2010 | Shah | ....................... | G01R 1/22 324/126 |
| 2011/0015796 A1 * | 1/2011 | Heydron | .................. | G05F 1/66 700/286 |
| 2011/0226063 A1 * | 9/2011 | Gysling | .............. | G01F 25/0007 73/623 |
| 2012/0169324 A1 * | 7/2012 | Worones | .................. | G01R 1/22 324/126 |
| 2015/0160053 A1 * | 6/2015 | Baumoel | ................. | G01F 1/667 73/861.28 |
| 2015/0267848 A1 * | 9/2015 | Zaharis | ................. | F16L 33/025 24/20 CW |
| 2015/0338186 A1 * | 11/2015 | Hopkins | ................. | F41C 23/14 42/73 |
| 2017/0074695 A1 * | 3/2017 | Baecke | .............. | A61M 16/021 |
| 2017/0225388 A1 | 8/2017 | Hasific | | |
| 2017/0361538 A1 | 12/2017 | Hasific | | |
| 2019/0111395 A1 * | 4/2019 | Greenizen | ................. | B25B 5/14 |

* cited by examiner

FASTENING DEVICE FOR MEASURING APPARATUSES ON PIPES

CROSS-REFERENCE TO RELATED APPLICATIONS

This application claims the benefit and priority of EP 18 165 894.9 filed Apr. 5, 2018. The entire disclosure of the above application is incorporated herein by reference.

FIELD

The invention relates to a device for fastening a measuring apparatus on pipes, in particular a butt weld seam checking measuring apparatus containing a housing for accommodating the measuring, control, and/or drive units and a clamp.

BACKGROUND

Such devices are primarily known for ultrasound measurements with respect to a flow rate measurement, wherein in general such measuring apparatuses are fastened using simple clamping systems or a pipe clamp on the pipe, wherein devices such as these generally do not have to be rotated on the pipe circumference or moved into another position.

WO 2011/112946 A1 discloses a device for flow rate measurement, wherein the measuring apparatus has two housings on the pipe circumference, wherein the two housings are fastened on the pipe by means of two rings.

The above-mentioned solution and also the solution known from the prior art have the disadvantage that the mounting is relatively complex and cumbersome, so that a greater time expenditure is required and tools are also usually necessary for this purpose.

SUMMARY

It is an aspect of the invention to propose a device which enables rapid and simple mounting of a measuring apparatus, in particular a weld seam checking measuring apparatus, on a pipe external diameter, without tools being necessary, and nonetheless the device is arranged in a twist-locked manner on the pipe but the device is also manually adjustable along the circumference. Moreover, the device is to be mountable with one hand and also only one handle is to be necessary for the mounting and complex lashing or clamping in place are to be avoided.

This aspect is achieved according to the invention in that the clamp is designed as a ring segment, wherein the clamp is attached in the radial direction over a pipe external diameter, wherein the clamp has a pre-tension in the installed state.

The device according a preferred embodiment of the invention for fastening a measuring apparatus on pipes, in particular a butt weld seam checking measuring apparatus, has a housing for accommodating the measuring, control, and drive units. All required components for carrying out a measurement are arranged therein, in dependence on the desired measurement. Preferably, a sensor, a circuit board, an illumination unit, a mirror, and a positioning drive are arranged during an application in the region for checking a weld seam, wherein further components or other components can also be arranged in the housing. The device moreover has a clamp which is used for fastening the device on the pipe. The clamp is clipped onto the pipe external diameter by radial pressing on, as a result of which the clamp has a wraparound angle which is greater than 180° and the ends of the clamp are thus pressed apart during the radial attachment on the pipe and press against one another again in the final position on the pipe external diameter, in particular to prevent undesired twisting with a pre-tension.

It is advantageous if the ring segment has a wraparound angle of greater than 180°, preferably a wraparound angle of 190-280°. It is thus ensured that the device is fixedly installed on the pipe external diameter, but is manually rotatable around the pipe external diameter or circumference and is axially displaceable along the pipe external diameter as needed.

The housing and the clamp are preferably formed as separate parts. This is accompanied by the advantage that only one housing having the corresponding measuring apparatus is required, which can then be fastened on different pipe diameters or on the corresponding clamps, which are designed for the corresponding pipe diameters. The housing is thus universally designed for all clamps for the different pipe dimensions. It is advantageous if the housing and/or the clamp are each produced in the injection moulding method or by additive manufacturing.

To enable the fastening of the device or the clamp on the pipe external circumference, it is advantageous if the material of the clamp is elastic. The clamp is preferably produced from plastic. The housing is also preferably produced from plastic.

It has been shown to be a preferred embodiment if the housing is fastened by means of a quick-acting closure on the clamp, preferably by a snap closure. It is advantageous if the housing has corresponding recesses on two opposing sides, in which, for example, a cam which is arranged on the clamp engages and a tab which can be tensioned, in the opposing recess, which positions and fixes the housing on the clamp.

The clamp preferably consists of two ring segments extending in parallel, which are connected to one another by means of at least one web. A recess thus results between the ring segments, which enables the device to be appropriately positioned axially, since the pipe and also the weld seam is thus visible between the ring segments. Moreover, the recess is also used so that the access to the pipe or the weld seam is ensured to the measuring apparatus.

It has been shown to be a preferred embodiment if the housing and the clamp are connected to one another in a formfitting manner, preferably by means of the cam of the snap closure and corresponding recess which accommodates the cam and thus ensures unique positioning of the housing on the clamp.

It is advantageous if the clamp has markings which indicate the measurement position, these markings are preferably situated laterally on the ring segments.

It has been shown to be a preferred embodiment if markings are indicated at a specific angle in relation to one another on the ring segment. In the case of measurements in which the device has to be rotated, it can therefore be accurately determined by which angle the device was rotated on the pipe external diameter if a marking was correspondingly provided on the pipe. A marking is preferably arranged at the 90° angle on the ring segment.

DRAWINGS

Figure 2:
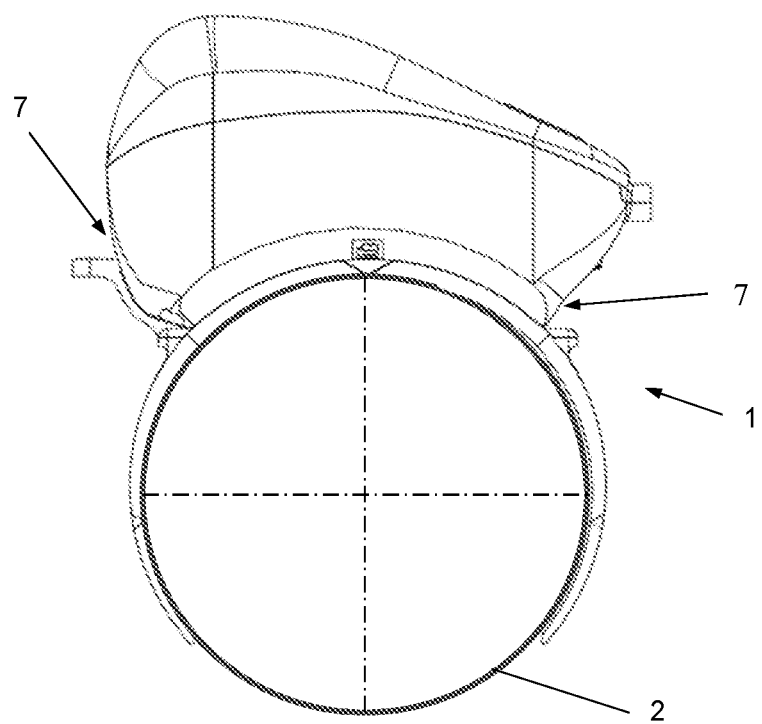
Figure 3:
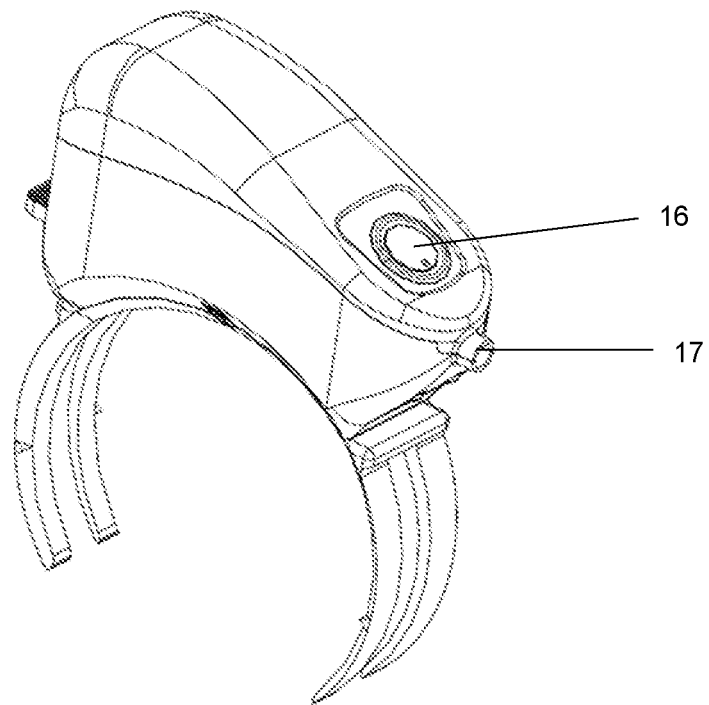
Figure 4:
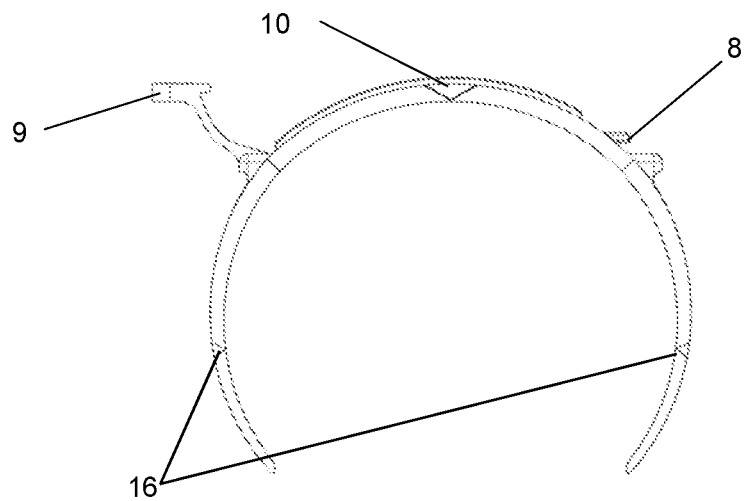
Figure 5:
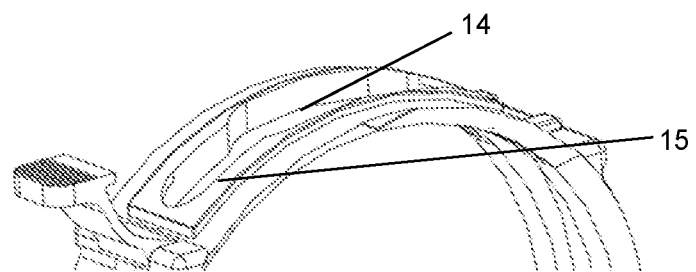
Figure 6:
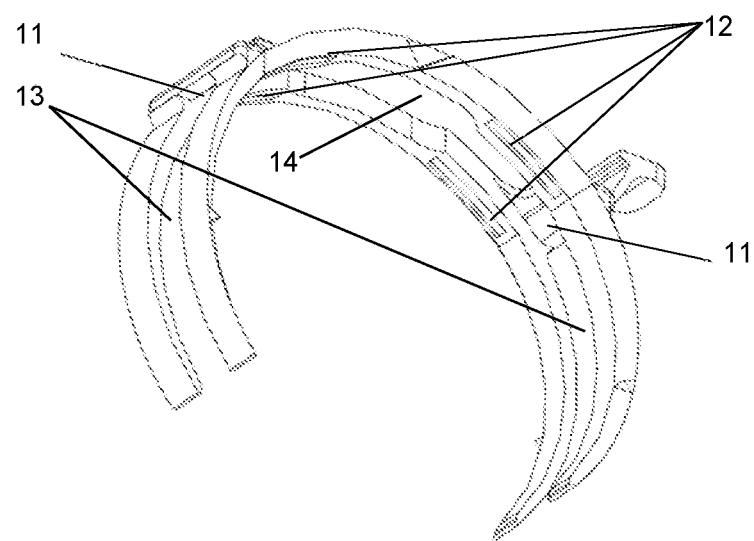
Figure 7:
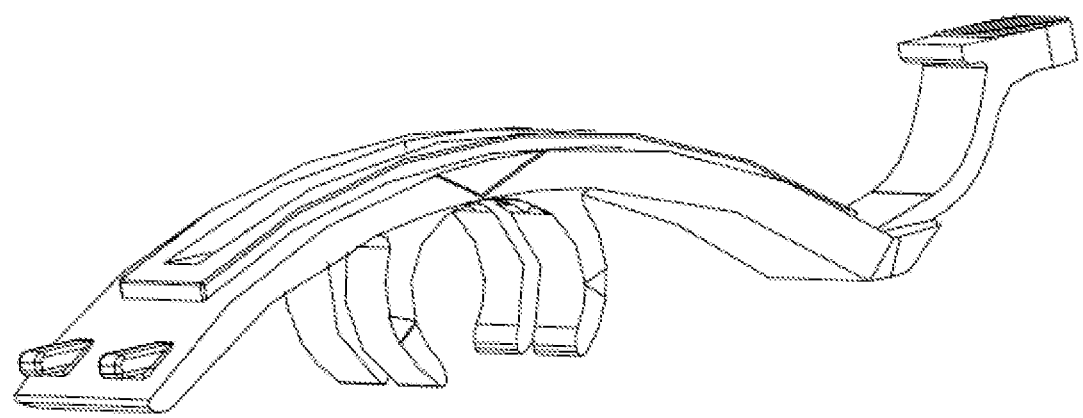
Figure 8:
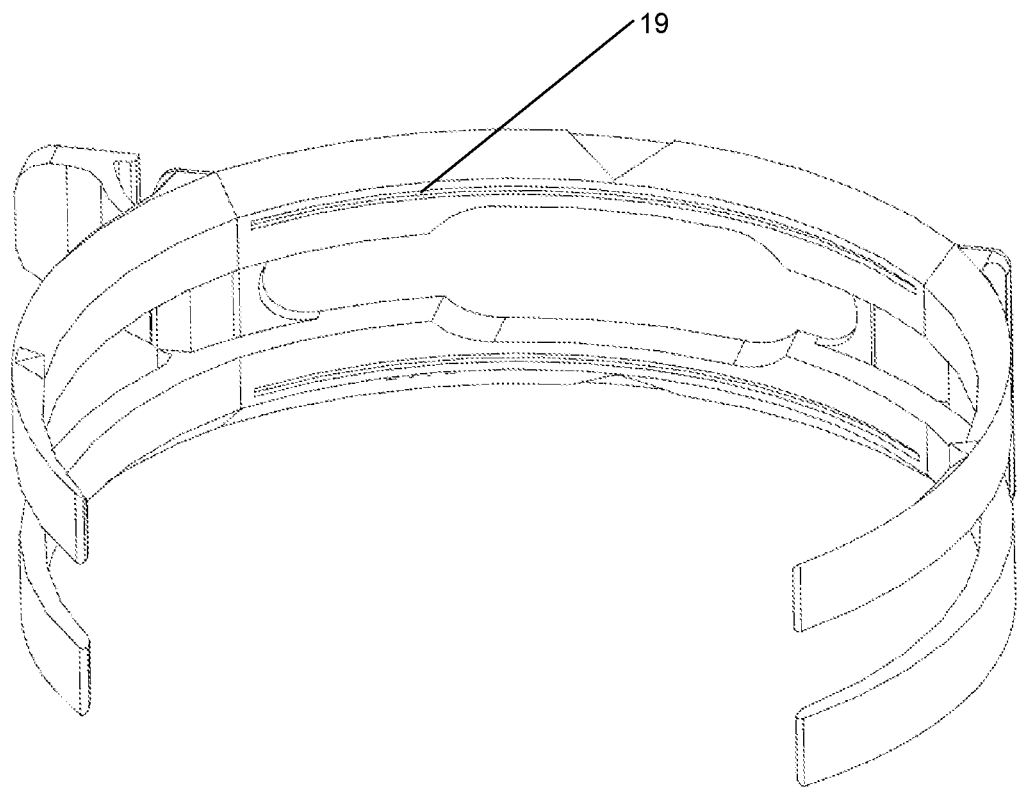

An exemplary embodiment of the invention will be described on the basis of the figures, wherein the invention is not only restricted to the exemplary embodiment. In the figures:

FIG. 1 shows a view during the mounting of the device according to the invention, FIG. 2 shows a view of the device according to the invention mounted on the pipe, FIG. 3 shows a three-dimensional view of a device according to the invention, FIG. 4 shows a view of a clamp of the device according to the invention, FIG. 5 shows a partial view of a clamp of the device according to the invention, FIG. 6 shows a three-dimensional view of a clamp of the device according to the invention, FIG. 7 shows a three-dimensional view of a clamp of the device according to the invention for a small pipe diameter, and FIG. 8 shows a three-dimensional view of a clamp of the device according to the invention having grooves instead of pockets.

DETAILED DESCRIPTION

The drawing shown in FIG. 1 shows a device 1 according to the invention for fastening a measuring apparatus on a pipe 2 having a housing 3 in which the measuring apparatus is arranged or the units required for this purpose in accordance with the measurement to be carried out are arranged, wherein FIG. 1 shows the device 1 during the mounting. It can be seen well therein that the device 1 is pressed or clipped onto the pipe 2 in the radial direction 5. Because the clamp 4 has a wraparound angle of greater than 180°, the ring segments 4 are spread apart as they are pressed on over the pipe diameter and then press against the pipe external circumference 2 when the device 1 is fastened on the pipe 2. Because the internal diameter of the clamp 4 is smaller than the pipe external diameter, the clamp 4 has a pre-tension in the state mounted on the pipe 2, whereby undesired displacement or twisting is avoided. FIG. 2 shows the device according to the invention, which is already fastened on the pipe 2.

The housing 3 is fastened by means of quick-acting closure or snap closure 6 on the clamp 4, wherein the tab 9 of the snap closure and the cam 8 engage in the recesses 7, as can be seen in FIG. 4, whereby the housing 3 is fastened in a formfitting manner on the clamp 4 or on the ring segment.

The clamp 4 is preferably formed by two ring segments extending in parallel, which are connected to one another by means of at least one web 11. Recesses 13, 14 are thus formed between the ring segments, which are used in the upper region or in the region on which the housing 3 is fastened for the accessibility of the measuring apparatus to the pipe, whereby a sensor can directly or indirectly acquire the pipe external diameter or circumference or the weld seam. Moreover, the recess in the lower region or after the two webs 11 is used so that during the attachment of the device 1 on the pipe external diameter, a rough, manual alignment in the axial direction can be performed, for example, by placing the weld seam to be checked approximately in the middle of the recess. Moreover, the edges on the ring segments, which are oriented in the direction of the recesses 13, 14, are used as a stop or guide of the weld seam, whereby the weld seam would line up at the edges and no displacement of the clamp 4 is possible. In the region in which the housing 3 is fastened on the clamp 4, the clamp 4 or the ring segments has/have a reinforcement 15 or a protrusion. This is used for light protection or shielding from the surroundings, whereby the measuring apparatuses cannot be impaired by incident light.

Moreover, the clamp 4 preferably has a marking 10 of the measuring position, which is also used for adjusting the device 1 according to the invention Furthermore, it is advantageous if markings 10 are arranged at a specific angle in relation to one another on the clamp 4, these enable the controlled rotation of the device 1 along the pipe circumference, whereby a measurement can always take place at a specific angle in relation to the other measurement A marking at an angle of 90° is preferably to be selected, whereby other positions of the markings are also conceivable.

The housing 3 preferably has an operating unit 16, which is kept as simple as possible, for example, by only one button which triggers different actions by various types of actuation. Moreover, it is advantageous if the operating unit has a display, preferably an LED, which indicates the operating state.

Moreover, the housing 3 preferably has a connecting unit, which enables an external controller to be attached, of course, a wireless connection to control units such as PCs is also conceivable.

It is advantageous if pockets 12 are arranged on the internal diameter of the clamp 4, which are used for accommodating, for example, rubber elements, which have a higher friction resistance and thus suppress an undesired pivot of the device 1.

A further embodiment of the clamp is shown in FIG. 8, in which a continuous groove 19 extends along the ring segment instead of the pockets, wherein the groove 19 preferably extends in the region in which the housing 3 is fastened and is arranged in both ring segments extending in parallel. A sealing profile can be arranged in the groove 19, which increases the friction resistance between pipe and clamp 4, on the one hand, and is also used as light protection or for shielding from the environment for the sensor in the housing 3, so that incident light does not influence the capture of the measurement data.

What is claimed is:

1. A device for fastening a measuring apparatus on a pipe comprising a housing for accommodating measuring, control, and/or drive units and a clamp having a pair of elastic ring segments with spaced apart ends, wherein the clamp is attached in the radial direction without tools over a pipe external diameter by pressing the ends over the pipe and clamping the ring segments around the pipe while maintain a recess between the ends of the segments, and wherein the clamp has a pre-tension in the installed state; and wherein the housing and the clamp are separate parts, with housing being configured to be removably attached to clamps of different ring segment sizes so that the same housing can be used with different clamps for pipes of different sizes.

2. The device according to claim 1, wherein the ring segments have a wraparound angle of greater than 180°.

3. The device according to claim 1, wherein the housing is fastened by a snap closure.

4. The device according to claim 1, wherein the clamp has two ring segments extending in parallel, which are connected to one another by means of at least one web, wherein the clamp is formed in one piece.

5. The device according to claim 1, wherein the housing and the clamp are connected to one another in a formfitting manner, by a cam on the clamp or housing and recess on the clamp or housing for receiving the cam.

6. The device according to claim 1, wherein markings, which indicate the measurement position, are arranged on the clamp.

7. A device for measuring pipes comprising:
- a set of clamps, each clamp having a pair of elastic ring segments with spaced apart ends, the ring segments defining an internal diameter, each clamp being attachable in the radial direction without tools over a pipe external diameter by pressing the ends over the pipe and clamping the ring segments around the pipe while maintaining a recess between the ends of the segments, the ring segments of different clamps defining different internal diameters;
- a housing for accommodating measuring, control, and/or drive units; and
- wherein the same housing is configured to be removably mounted to each of the clamps whereby the same housing can be used to measure pipes of different diameters using a clamp configured for a particular pipe diameter.

8. The device according to claim 7, wherein the housing and the clamp are connected to one another in a formfitting manner, by a cam on the clamp or housing and recess on the clamp or housing for receiving the cam.

* * * * *